United States Patent [19]

Kundsin

[11] Patent Number: 5,767,163

[45] Date of Patent: *Jun. 16, 1998

[54] LUBRICATING AND/OR GERMICIDAL COMPOSITION

[75] Inventor: Ruth B. Kundsin, Squantum, Mass.

[73] Assignee: Kundsin Leduc Lenmark Inc., Minneapolis, Minn.

[*] Notice: The term of this patent shall not extend beyond the expiration date of Pat. No. 5,492,932.

[21] Appl. No.: 602,581

[22] Filed: Feb. 16, 1996

Related U.S. Application Data

[63] Continuation-in-part of Ser. No. 199,335, Feb. 22, 1994, Pat. No. 5,492,932.

[51] Int. Cl.$^6$ .................... A61K 31/14; A61K 31/19; A61K 31/045; A61K 7/48
[52] U.S. Cl. .................... 514/642; 514/557; 514/558; 514/724; 514/844; 514/846; 514/847; 514/873
[58] Field of Search .................... 514/557, 558, 514/642, 724, 844, 846, 847, 873

[56] References Cited

U.S. PATENT DOCUMENTS

| | | | |
|---|---|---|---|
| 3,879,537 | 4/1975 | Van Scott et al. | |
| 4,105,782 | 8/1978 | Yu et al. | 424/283 |
| 4,143,159 | 3/1979 | Moller et al. | |
| 4,197,316 | 4/1980 | Yu et al. | 424/317 |
| 4,294,852 | 10/1981 | Wildnauer et al. | |
| 4,316,902 | 2/1982 | Yu et al. | |
| 4,363,815 | 12/1982 | Yu et al. | 424/274 |
| 4,975,217 | 12/1990 | Brown-Skrobot et al. | 252/109 |
| 5,008,030 | 4/1991 | Cook et al. | 252/106 |
| 5,492,932 | 2/1996 | Kundsin | 514/642 |

OTHER PUBLICATIONS

Kundsin, "Investigations on Dynamics of Bactericidal Action of Two Quaternary Ammonium Salts", *Archives of Surgery*, 81:789–797 (1960).

Kundsin, "Problems and Techniques of Floor Sanitation", Paper Presented at Chemical Specialties Manufacturers Assocation Meeting in Chicago, (May 15, 1962).

Kundsin et al., "Antiseptics and Disinfectants", *The Practitioner Symposium on Clinical Pharmacology*, 200:15–22 (1968).

Walter et al., "The Bacteriologic Study of Surgical Gloves from 250 Operations", *Surgery, Gynecology & Obstetrics*: 129:949–952 (1969).

"Hand Cream Kills HIV, Other Viruses, Firm Says", *Florida Times Union*, Jacksonville, p. A–15 (Thursday, Dec. 17, 1992).

"Viroglove", Product Literature (1992).

*Physicians Desk Reference*, V.R. Arky, ed., Medical Economics Data Production Co., Montvale, pp. 893, 894, 1746, 2171–2173 (1992).

*Primary Examiner*—Shep K. Rose
*Attorney, Agent, or Firm*—Merchant, Gould, Smith, Edell, Welter & Schmidt, P.A.

[57] ABSTRACT

The present invention is directed to a lubricating and/or germicidal composition, and a method of using the composition as an antiseptic for the hands or as a disinfectant for other inanimate objects, and/or for alleviating or preventing drying of skin. The composition is an alcoholic solution containing cetyl alcohol, glycolic acid, benzalkonium chloride, and a major amount of isopropyl alcohol. In a preferred use, the composition is applied to the surface of the hands as an antiseptic film or "invisible glove" beneath a surgical or other plastic glove to inhibit microbial growth and alleviate drying of the skin.

26 Claims, No Drawings

LUBRICATING AND/OR GERMICIDAL COMPOSITION

CROSS-REFERENCE TO RELATED APPLICATION

This is a continuation-in-part of U.S. patent application Ser. No. 08/199,335, filed Feb. 22, 1994, to issue as U.S. Pat. No. 5,492,932 (Feb. 20, 1996).

BACKGROUND OF THE INVENTION

Bacteria from the hand of a surgeon or other operating room personnel can be the source of serious infections in surgery patients. While transfer of bacteria is substantially reduced by routine surgical scrubbing procedures, it is prudent to take additional steps to eliminate bacteria and other microorganisms that may grow under surgical gloves. If left unchecked, these organisms could escape through an all too common puncture to the glove and infect the patient. To this end, a germicidal solution is often coated onto the hands before slipping on surgical gloves. Optimally, the coating remains on the skin surface of the hands during a surgical operation to inhibit bacterial growth of bacteria. However, current germicidal solutions cause significant drying of the skin, and do not provide a coating which allows for easy donning or removal of surgical gloves.

Therefore, an object of the present invention is to provide a composition which is an effective germicide with a high level of moisturizing activity on the skin of the user. Another object is to provide an effective germicidal composition which may be coated onto skin to provide an antiseptic film which will allow for ready placement and removal of gloves over the skin. Yet another object is to provide a composition that is useful for lubricating the skin to inhibit drying.

SUMMARY OF THE INVENTION

These and other objects are achieved by the present invention which is directed to a lubricating and/or germicidal composition, and a method of using the composition as an antiseptic lotion for the hands or a disinfectant for inanimate objects, and/or for alleviating or preventing drying of skin.

The composition contains isopropanol, a germicidally-active quaternary ammonium salt, cetyl alcohol and glycolic acid. The quaternary ammonium salt is an effective germicide for vegetative cells, fungi, algae and viruses. The combination of isopropanol and quaternary in the present composition provides substantially instant disinfection of a surface on contact, and a synergistic effect which increases the effectiveness of each of their respective activities as a germicide. In addition, the alcohol provides an initial fast-acting germicidal activity, and evaporates leaving a germicidal residue of the quaternary substantially evenly distributed over the surface for a lasting germicidal effect, particularly when the treated surface becomes wet. This feature provides a distinct advantage for retaining the composition on the treated surface in the event that the treated surface is contacted with an infectious material. The germicidal residue remains on the surface and will retain its activity on an undisturbed surface for up to about 1 year, or until the composition is removed by washing the treated surface, for example, with conventional soap and water.

The cetyl alcohol and glycolic acid in the composition act in combination to prevent drying of the skin following application of the alcohol and to add lubricity to the composition. The cetyl alcohol further acts as an emollient and emulsion modifier in the composition. The glycolic acid is a newly recognized cosmetic additive with moisturizing properties.

The invention further provides a method of inhibiting microbial growth on a substrate by contacting the surface of the substrate with the germicidal composition. The composition may be used as a disinfectant for countertops and other inanimate objects, or as an antiseptic lotion which is applied to the hands or other skin surface. The composition forms a protective germicidal barrier when applied to the skin or other hard surface. In a preferred use, the composition is used in conjunction with gloves or other protective outerwear that are utilized, for example, by a surgeon or other health care provider, a food handler, and the like. The composition provides a moisturizing germicidal film on the surface of the skin which act as an antiseptic "invisible glove" beneath a surgical or other plastic glove. In another preferred use, the composition is used for lubricating the skin to alleviate or prevent drying.

The invention also contemplates an article of manufacture, or kit, for use in inhibiting microbial growth on a substrate. The kit is composed of, in combination, the germicidal composition packaged within containing means, optionally with instruction means comprising information for the use of the composition and/or other related literature, a pair of surgical glove or other outerwear, and/or a cloth or other material for applying the composition.

DETAILED DESCRIPTION OF THE INVENTION

The invention provides a topical, lubricating and/or germicidal composition for applying to a substrate such as the hands or an inanimate object. The composition is an alcoholic solution containing cetyl alcohol, glycolic acid, benzalkonium chloride, and a major amount of isopropyl alcohol. The composition is an effective germicide against bacteria, fungus, yeast, and viruses, and/or for alleviating or preventing drying of the skin of the user.

Cetyl alcohol, a $C_{16}$ fatty alcohol, is included in the composition as an emulsifier and as a lubricant to allow gloves to be more easily slipped onto and off of the hands. The composition contains about 1–25 wt-% cetyl alcohol, preferably about 1–15 wt-%, preferably about 1–10 wt-%, preferably about 2–3 wt-%, preferably about 1.5–2.5 wt-%, more preferably about 2.5 wt-%.

The composition includes an effective bactericidal amount of benzalkonium chloride, a quaternary ammonium antimicrobial agent that is commercially available, for example, as Zephiran® chloride (Winthrop), 17% concentrate. The alkyl groups of the quaternary range from $C_8$ to $C_{18}$. The composition includes about 0.1–1.5 wt-% of the 17% solution of benzalkonium chloride, preferably about 0.1–1 wt-%, preferably about 0.1–0.8 wt-%, preferably about 0.1–0.5 wt-%, more preferably about 0.13%.

The composition is formulated with a major amount of isopropyl alcohol. Although not intended to limit the scope of the invention, it is believed that the isopropyl alcohol enhances the germicidal action of the remaining ingredients, particularly the bactericidal effects of the benzalkonium chloride. The isopropyl alcohol also provides for an even distribution of the ingredients over the skin or other substrate. The composition includes about 60–98% isopropyl alcohol, preferably about 70–98%, preferably 80–98%, more preferably about 90–98%, more preferably about 95%.

Surprisingly, it has been found that the combination of cetyl alcohol and glycolic acid with the other named ingredients provides a composition having a high level of germicidal activity with increased lubricating effects which enhance the feel of the composition on the skin of the user. The glycolic acid and cetyl alcohol act to prevent drying of the skin by the isopropyl alcohol in the composition. To achieve this level of activity, the composition includes an effective lubricating amount of glycolic acid, preferably about 0.1–3 wt-%, preferably about 0.1–1 wt-%, preferably about 0.1–0.4 wt-%, preferably about 0.2–0.4 wt-%, preferably about 0.2–0.3 wt-%, more preferably about 0.25 wt-%.

The composition may optionally include minor amounts of additive agents for specific uses as desired. The composition contains the ingredients in a concentration such that dilution by water on the skin or in spills of contagious material will not diminish or interfere with its effectiveness as a germicide.

The concentration of ingredients in the composition is effective to decrease the microbial count on the skin or other substrate by about 95–100% within about 5–40 seconds after contact, more preferably within about 5–10 seconds.

In a preferred embodiment of the invention, the composition is formulated with about 1–3 wt-% cetyl alcohol, about 0.1–0.4 wt-% glycolic acid, about 0.1–1 wt-% benzalkonium chloride, and about 90–98 wt-% isopropyl alcohol.

The present compositions exhibit improved efficacy as a combination germicide and moisturizing lotion, and have particular usefulness as an antiseptic lotion applied to the hands or other skin surfaces. The mixture of ingredients synergistically provide a germicidal effect and an improved moisturizing effect on the skin. The composition also enables gloves, such as surgical gloves and the like, to be more easily slipped over the skin.

The composition when dried on the skin remains intact as a film and provides a persistent residual germicidal coating on the surface of the skin until washed off. The composition may be removed by washing with a commercial hand soap or other like detergent. On a hard surface, undisturbed, the germicidal residue can last up to about one year.

The compositions are an effective germicide against a wide assortment of microorganisms. The composition is effective in destroying gram-negative and gram-positive organisms on contact. For example, the composition may be used as an effective bactericide, for example, against *Staphylococcus aureus*, *Staphylococcus epidermidis*, *Salmonella cholerasuis*, *Escherichia coli*, *Klebsiella pneumoniae*, *Listeria monocytogenes*, *Streptococcus pyogenes*, *Enterobacter agglomerans*, *Serratia marcescens*, *Legionella pneumophila*, *Leucothrix mucor*, and *Mycobacterium tuberculosis*, and the like. The composition provides effective fungicidal action against organisms such as *Candida albicans*, *Trichophyton mentagrophytes*, *Aspergillus niger*, *Myrathecium verrucaria*, *Trichoderma viride*, *Chaetomium globosum*, and the like. The composition is also an effective algicide against algae such as *Stigeoclonium spp.*, *Oscillaturia tenuis*, *Anacystis cylindrica* and other like blue-green algae, and the like. In addition, the composition possesses effective virucidal activity against such viruses as hepatitis B virus, rhinovirus, parainfluenza virus, adenovirus, rabies, and human immunodeficiency virus (HIV), hydrophilic viruses such as Coxsackie virus, echo virus, and poliovirus, lipophilic viruses such as herpes simplex, vaccinia virus, and influenza virus, and the like. It is also effective in destroying cysts of protozoa such as *Entamoeba histolytica*.

The compositions are generally prepared by combining the ingredients in a suitable mixing vessel. The ingredients may be added simultaneously or sequentially, and mixed together to form an alcoholic solution. The compositions may be prepared at about room temperature (25° C.), and are stable for up to about 6–12 months when stored at about room temperature (25° C.).

The germicidal compositions of the invention are advantageously used by persons whose occupation requires them to wear gloves, for example, a surgeon, food handler, hair dresser, and the like. In use, the composition is applied topically to the hands, preferably following a pre-operative scrub-up or other hand wash with a detergent or antiseptic. The isopropyl alcohol is allowed to evaporate, wherein a film-like coating is formed on the surface of the skin. The composition remains on the surface of the skin for a period of time until washed off.

Advantageously, the composition may be retained on the skin to provide a continuous residual germicidal action over an extended period of time until washed off. To achieve such extended germicidal activity, a glove made of plastic, latex, rubber and the like, for example, a surgical glove, or other like outerwear, may be placed over the dried composition on the skin. The combination of ingredients provides a composition which will form a film on the skin surface which is smooth and slippery to the touch to allow gloves to be more easily slipped on and off the hands, thus facilitating a handling step where accidental bacterial contamination could occur. In addition, the ingredients, particularly the glycolic acid, reduces dehydration of the skin from wearing gloves over an extended period of time.

The composition may also be used as a disinfectant to disinfect inanimate objects such as countertops, examination tables, especially after spills of infectious material in a hospital or laboratory setting where hazardous wet spills are frequently encountered, and the like. In use, the substrate to be disinfected is contacted with the composition by spraying, wiping with a cloth or sponge, submersion in a container of the composition, and the like. The composition is allowed to remain on the surface of the object until it evaporates. The germicidal composition may remain on the object, or may be removed either by wiping or rinsing with soap and water. Additionally, the composition may be used as a rapid spray on hazardous spills of patient secretions, excretions, blood, and the like.

The germicidal composition may be packaged as an article of manufacture, or kit, for use in disinfecting inanimate objects and as an antiseptic lotion on skin surfaces. The kit includes, the composition packaged within containing means, for example, a foil or plastic pouch, or a vial, jar or other like container, optionally with means for spraying, or impregnated in a packaged absorbent fibrous or cellular sheet material which may be dropped, pressed, or rubbed onto the surface of the skin or object to release an effective amount of the composition thereon, and other like containers. The kit may further include instruction means composed of information relating to the use of the composition, pharmaceutical information, and other like literature, and/or, gloves such as surgeons gloves, and/or a cloth, tissue or other cellulosic material for spreading the composition onto a hard surface. The instruction means may be in the form of a label or tag attached to the packaging, or a printed package insert within the packaging and the like.

The invention will be further described by reference to the following detailed examples, wherein the methodologies are as described below. These examples are not meant to limit the scope of the invention that has been set forth in the foregoing description. Variation within the concepts of the invention are apparent to those skilled in the art. The disclosures of the cited references are incorporated by reference herein.

EXAMPLE I

Preparation of Germicidal Lubricating Lotion

A germicidal composition was prepared with the ingredients as shown in Table I, below.

TABLE I

|  | AMOUNT | WEIGHT % |
|---|---|---|
| Cetyl Alcohol | 2000 gm | 2.5% |
| Zephiran Concentrate (17%) | (615 ml) 104.55 gm | 0.13% |
| Glycolic Acid | 200 gm | 0.25% |
| Isopropyl Alcohol Q.S. | 80,000 ml | 96% |

To prepare a germicidal lotion, 2000 grams cetyl alcohol (Ciba-Geigy Corp., Woodbridge, N.J.), 250 grams glycolic acid (hydroxyacetic acid; Aldrich Chemical Company) and 615 ml benzalkonium chloride (Zephiran chloride, concentrate, 17%; Winthrop Pharmaceuticals, New York, N.Y.) were dissolved in isopropyl alcohol (99%) and mixed at room temperature until enough isopropyl alcohol was added to the mixture to form a 80 liter solution.

The final composition contained 2.5% cetyl alcohol, 0.13% benzalkonium chloride, 0.25% glycolic acid, and 96% isopropyl alcohol (99%).

EXAMPLE II

Use of the Germicidal Lubricating Lotion as an Antiseptic

The composition prepared in Example 1 was applied to the surface of the hands to test its effectiveness against normal skin flora such as *staphylococci, micrococci*, and *diphtheroids*.

Samples of bacteria were taken from the surface of the hands prior to application of the composition. The composition (1–2 ml) was sprayed onto the hands as a thin coating. The isopropyl alcohol evaporated within 2–4 seconds, and the composition formed as an even, inconspicuous film on the skin surface. After 1.5 hours, samples were again taken from the skin surface. The bacterial counts before and after applying the composition is shown in Table II below.

TABLE II

|  | FINGER TIPS LEFT HAND | FINGER TIPS RIGHT HAND |
|---|---|---|
| Pre-Treatment | 102 | 37 |
| Post-Treatment[1] | 5 | 1 |
| % Reduction | 95% | 97% |

[1]Following wetting of the hand with 1–2 ml of the composition and allowing the composition to air dry.

What is claimed is:

1. A composition, comprising:
   (a) about 1–25 wt-% cetyl alcohol;
   (b) an effective lubricating amount of glycolic acid;
   (c) an effective bactericidal amount of benzalkonium chloride; and
   (d) a major amount of isopropyl alcohol; the combination of isopropyl alcohol, glycolic acid and benzalkonium chloride being germicidally effective.

2. The composition according to claim 1, comprising about 1–10 wt-% cetyl alcohol.

3. The composition according to claim 1, comprising about 0.1–3 wt-% glycolic acid.

4. The composition according to claim 3, comprising about 0.2–0.3 wt-% glycolic acid.

5. The composition according to claim 1, comprising about 60–98% isopropyl alcohol.

6. The composition according to claim 1, comprising about 90–98% isopropyl alcohol.

7. The composition according to claim 1, comprising about 0.1–1.5 wt-% benzalkonium chloride.

8. The composition according to claim 7, comprising about 0.1–0.5 wt-%, benzalkonium chloride.

9. The composition according to claim 1, wherein the composition is effective in inhibiting the growth of a microorganism selected from the group consisting of gram-positive bacteria, gram-negative bacteria, fungi, viruses, alga, and any combination thereof.

10. The composition according to claim 1, wherein the composition is effective in alleviating or preventing drying of the skin.

11. The composition according to claim 10, wherein the composition is effective against a bacteria selected from the group consisting of *Staphylococcus aureus, Staphylococcus epidermidis, Salmonella cholerasuis, Escherichia coli, Klebsiella pneumoniae, Streptococcus pyogenes, Enterobacter agglomerans, Serratia marcescens, Legionella pneumophila, Listeria monocytogenes, Leucothrix mucor, Mycobacterium tuberculosis*, and any combination thereof.

12. The composition according to claim 11, wherein the composition is effective against a fungus selected from the group consisting of *Candida albicans, Trichophyton mentagrophytes, Aspergillus niger, Myrathecium verrucaria, Trichoderma viride*, and *Chaetomium globosum*, and any combination thereof.

13. The composition according to claim 11, wherein the composition is effective against an alga selected from the group consisting of *Stigeoclonium spp., Oscillaturia tenuis*, any *Anacystis cylindrica*.

14. The composition according to claim 11, wherein the composition is effective against a virus selected from the group consisting of rhinovirus, parainfluenza virus, adenovirus, rabies, human immunodeficiency virus, Coxsackie virus, echo virus, poliovirus, herpes simplex, vaccinia virus, influenza virus, and any combination thereof.

15. The composition according to claim 11, wherein the composition is effective against *Entamoeba hystolytica*.

16. The composition according to claim 1, comprising:
   (a) about 1–25 wt-% cetyl alcohol;
   (b) about 0.1–3 wt-% glycolic acid;
   (c) about 0.1–1.5 wt-% of benzalkonium chloride; and
   (d) about 60–98 wt-% isopropyl alcohol.

17. A method of disinfecting skin, comprising: contacting the skin with the composition of claim 1.

18. The method according to claim 17, wherein the method further comprises:
   allowing the composition to dry to a film on the skin; and
   maintaining the composition on the skin for a time effective to deliver a germicidal effect to the skin.

19. The method according to claim 17, wherein the substrate is the skin of a hand, and the method further comprises applying a glove onto the hand over the composition.

20. A method of lubricating and inhibiting drying of skin, comprising: contacting the skin with the composition of claim 1.

21. The method according to claim 20, further comprising:

allowing the composition to dry to a film on the skin; and maintaining the composition on the skin for a time effective to deliver a lubicating effect to the skin.

22. An article of manufacture comprising the composition of claim 1 packaged within containing means, and instruction means for using the composition for inhibiting the growth of a microorganism on human skin or an inanimate object, or for lubricating the skin to inhibit drying, or a combination thereof.

23. The article according to claim 22, wherein the containing means is selected from the group consisting of a vial, jar, pouch, absorbent fibrous sheet, or any combination thereof.

24. The article according to claim 23, wherein the containing means comprises means for spraying.

25. The article according to claim 22, wherein the instructions means is a label or tag attached to the packaging, a printed package insert, or a combination thereof.

26. The article according to claim 22, further comprising a plastic glove, a material for applying the composition to a substrate, or a combination thereof.

* * * * *